United States Patent [19]

McCall

[11] Patent Number: 4,483,021
[45] Date of Patent: Nov. 20, 1984

[54] THERMO-ELECTRIC COOLED HEAD GEAR

[75] Inventor: Jerry C. McCall, Gulfport, Miss.
[73] Assignee: Mckool, Inc., Gulfport, Miss.
[21] Appl. No.: 405,636
[22] Filed: Aug. 5, 1982
[51] Int. Cl.³ ............................................... A42B 3/00
[52] U.S. Cl. .......................................... 2/7; 128/399
[58] Field of Search ......................... 2/7, 410, 425, 424, 2/10, 422, 171.3; 62/3, 259.3; 128/399, 400, 402

[56] References Cited

U.S. PATENT DOCUMENTS

| | | |
|---|---|---|
| 3,070,803 | 1/1963 | Slepicka . |
| 3,132,688 | 5/1964 | Nowak . |
| 3,295,522 | 1/1967 | Johnson ........................... 128/399 X |
| 3,314,242 | 4/1967 | Lefferts ................................. 62/3 |
| 3,391,407 | 7/1968 | Waters ................................ 2/171.3 |
| 3,548,415 | 12/1970 | Waters ................................ 2/171.3 |
| 4,115,874 | 9/1978 | Hasegawa ....................... 2/171.3 X |
| 4,133,055 | 1/1979 | Zebuhr . |
| 4,172,495 | 10/1979 | Zebuhr et al. .................. 128/400 X |
| 4,338,944 | 7/1982 | Arkans ............................ 128/402 X |
| 4,354,284 | 10/1982 | Gooding . |

FOREIGN PATENT DOCUMENTS 0050473 4/1982 European Pat. Off. ................ 2/410

*Primary Examiner*—Peter P. Nerbun
*Attorney, Agent, or Firm*—Griffin, Branigan & Butler

[57] ABSTRACT

A motorcycle helmet defines a cavity in a hard fiber shell. A thermo-electric heat pump is mounted in the cavity, and a light metal radiator is bonded to both shell and pump. One way conductors energize the heat pump from a motorcycle battery source to pump heat from the hard fiber shell to the radiator. A flexible blatter filled with heat transfer liquid is mounted in the hard fiber shell and below the heat pump and in thermal contact with a wearer's head and the heat pump, for conducting head heat to the pump to electrically pump to the radiator for radiation to the atmosphere.

8 Claims, 4 Drawing Figures

THERMO-ELECTRIC COOLED HEAD GEAR

BACKGROUND OF THE INVENTION

The invention generally comprises temperature or air conditioned safety helmets and more particularly thermo-electric cooled motorcycle helmets.

The prior art discloses air conditioning a safety helmet by evaporation of liquid, such as in Waters U.S. Pat. No. 3,548,415 and the use of a small electrically energized fan. Thermo-electric cooling is taught by Lefferts, U.S. Pat. No. 3,314,242 for use in scientific laboratories and in exothermic reactions.

The present invention teaches cooling a safety helmet with a thermo-electric heat pump adapted to and installed in said safety helmet in accordance with Federal Motor Vehicle Standards.

SUMMARY OF THE INVENTION

It is an object of the invention to adapt the teaching of a natural law, as disclosed by the Seebeck, Peltier, and Thomson effects, to the cooling of a motorcycle helmet as Lefferts did to the heating and cooling of portable heating and cooling devices for laboratory use.

Another object of the invention is to cool a motorcycle safety helmet with electrical means and without moving parts.

The foregoing and other objects of the invention will be apparent from the following disclosure, drawings and claims.

DETAILED DESCRIPTION OF THE INVENTION

Figure 1:
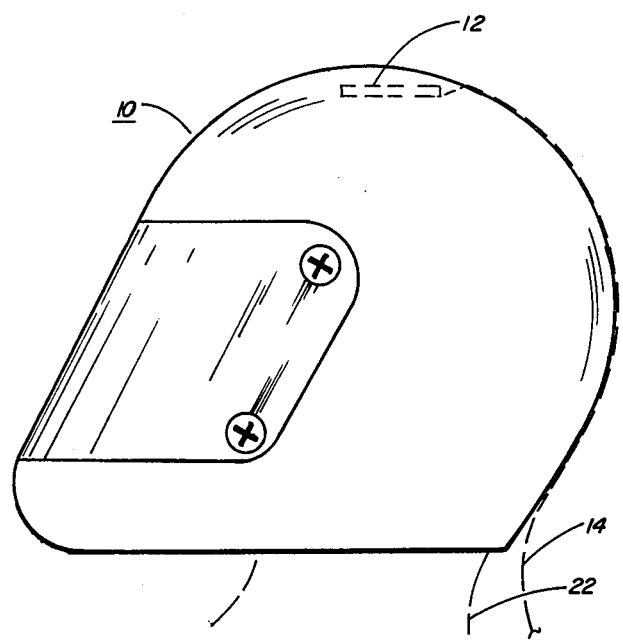
FIG. 1 is a side view of a motorcycle safety helmet with thermo-electric heat pump and connecting wires in dashed lines indicating interior mounting.
Figure 2:
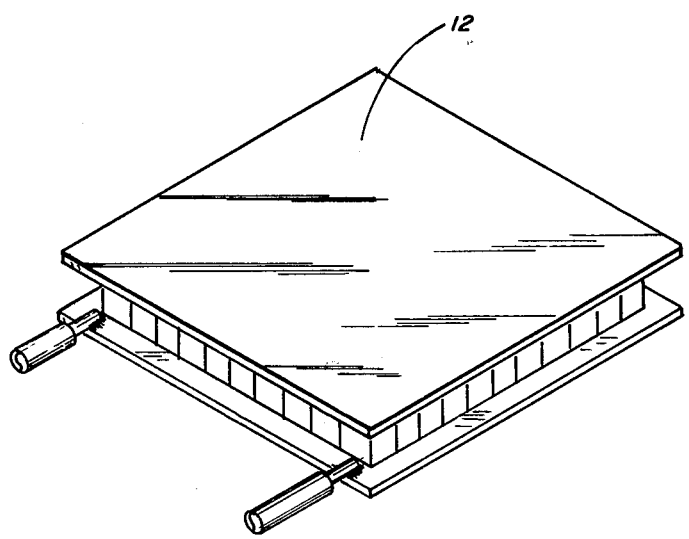
FIG. 2 is a three dimensional drawing of a thermo-electric heat pump.
Figure 3:
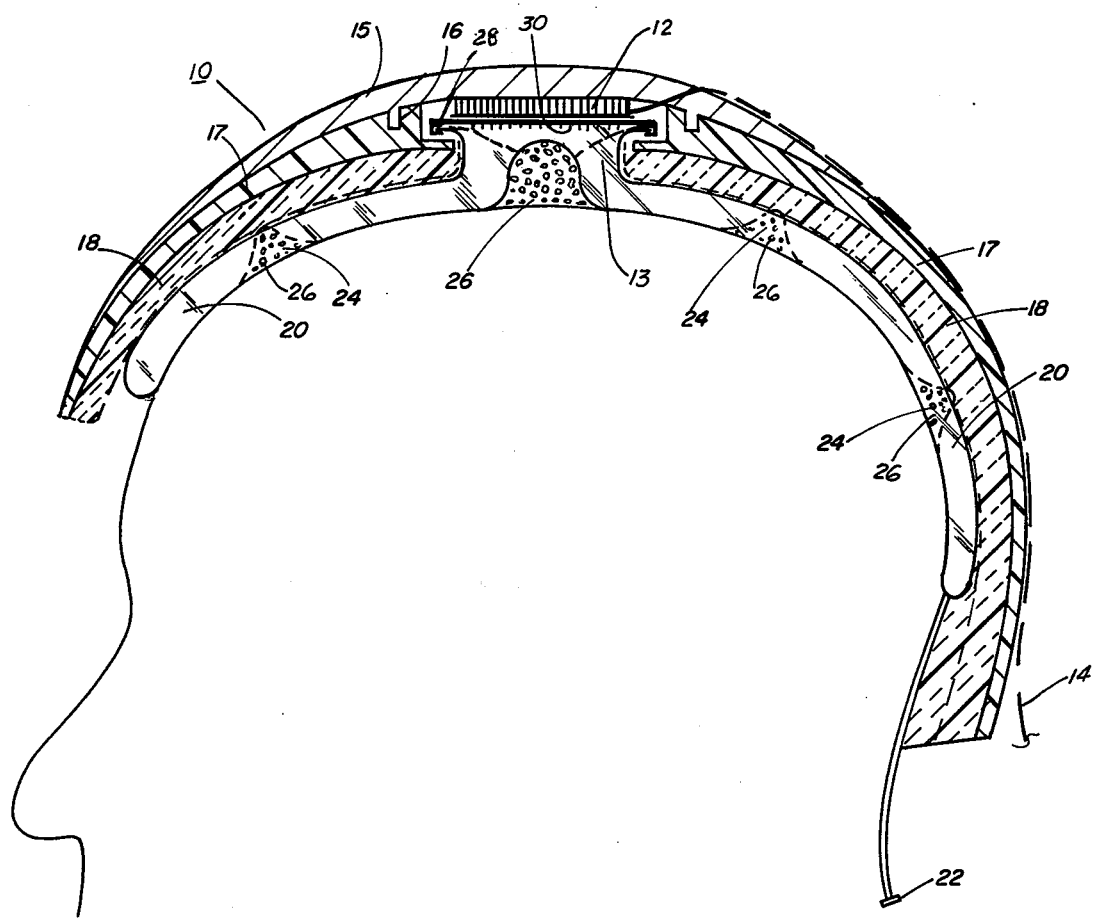
FIG. 3 is a longitudinal cross sectional view of the helmet of FIG. 1 along section line 3—3.
Figure 4:
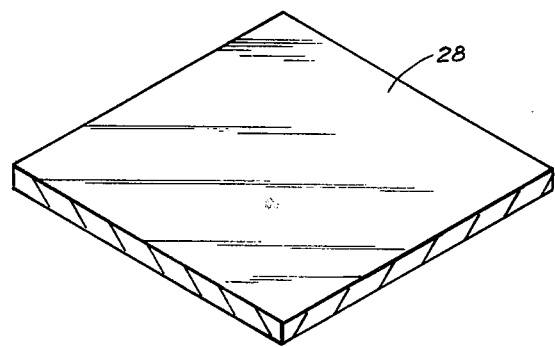
FIG. 4 is a three dimensional view of a bladder top.

Referring to FIGS. 1-4, a safety motorcycle helmet 10 completely encloses the head of a wearer and is very hot to wear. A heat pump 12, having upper hot and lower cold plates, is mounted in a cavity 13 defined in the top of helmet 10. Insulated electrical conductors 14 connect heat pump 12 to a motorcycle battery (not shown). A radiator shell 15 is fixed by anchor pins 16 and bonding to a hard fiber helmet shell 17 for the double purpose of closing said cavity 13 and for radiating heat from heat pump 12 upper hot plate. A hard foam helmet liner 18, defining a continuation of cavity 13, is bonded to the inner surface of hard fiber shell 17. An elastic bladder 20 is bonded to foam liner 18 and extends upwardly into the cavity 13. The bladder 20 has a filler tube 22 extending downwardly in helmet 10 for filling said bladder with a heat transfer liquid, preferably water in temperate climes. Bladder 20 is also attached to foam liner 18 to form dimples 24 along bladder centerline without blocking passage on either side of the dimples of heat transfer liquid convection currents. Sponges 26 are pressed into dimples 24 and into cavity 13 below bladder 20 to respectively maintain the shape of the dimples 24, and to support bladder in the cavity. A square metal top or cover 28, having depending fins 30, closes the upwardly extending opening of the bladder. Cover 28 is dimensioned to precisely conform with the bottom of heat pump 12 to which it is bonded making heat transfer liquid to metal to metal contacts for the more efficient transfer of heat thereby.

In operation, electrical conductors 14, one of which includes a diode for restricting a flow of current to one direction only, is engaged through a connector (not shown) to a motorcycle battery for the one way current to flow to cool the lower plate side of heat pump 12 that is bonded to bladder square top 28. Helmet wearer's head heat is transferred by direct contact to bladder 20 to heat transfer liquid contained therein, to bladder top cover 28 to said cooled lower plate and is electrically pumped to said upper hot plate and transferred by contact with radiator shell 15 to ambient atmosphere and dispersed therefrom by airflow around helmet 10.

The helmet of the invention conforms to all Federal Motor Vehicle Safety Standards and Regulations FMVSS No. 218 Motorcycle Helmets, and particularly with restrictions of projections above and below said hard fiber shell 17.

Electro-thermal pumps are obtainable from Marlow Industries Inc., 1021 S. Jupiter Road, Garland, Tex. 75042.

What is claimed is:

1. Thermo-electric cooled headgear comprising:
   (a) a hard shell having a cavity defined in and through said hard shell;
   (b) thermo-electric heat pump means mounted in said cavity;
   (c) thermal radiation means closing said cavity and extending along a portion of the exterior of said shell, said thermal radiation means being connected to said heat pump means whereby heat is transferred by said heat pump means through said cavity and from said heat pump means for heat radiation from said radiation means;
   (d) insulated electrical conduction means operationally connected to said heat pump means and connectable to an electrical power source for energizing said heat pump to electrically pump heat to said radiation means, and;
   (e) liquid heat transfer means mounted in said headgear for transfering heat between a wearer's head and said heat pump, said liquid heat transfer means comprising bladder means conformable in shape to the contour of a wearer's head, said bladder means being fillable with a heat transfer liquid whereby heat transfer liquid convection currents transfer heat from the wearer's head, around said contour, and to said heat pump means.

2. The headgear of claim 1 wherein said thermal radiation means comprises:
   (a) a hardened, light-metal radiation member secured to said hard shell by bonding and press-engaging pins into said hard shell.

3. The headgear of claim 1 wherein said electrical conduction means comprises:
   (a) a one-way flow diode connected therein.

4. The headgear of claim 1 wherein said liquid heat transfer means comprises:
   (a) a flexible bladder fillable with a heat transfer liquid and connected to said heat pump means for bladder contact with a wearer's head and with said heat pump.

5. The headgear of claim 1 wherein said cavity is through the top of said shell, wherein said thermo-electric heat pump means is mounted in said cavity flush with the top of said shell, and wherein said thermal radiation means closes said cavity at the top of said shell.

6. The headgear of claim 1 wherein said headgear is for wear when riding a motorcycle, and wherein said insulated electrical conduction means is connectable to a motorcycle direct current electrical power source.

7. The headgear of claim 4 wherein said flexible bladder is mountable below said heat pump means. ,13

8. Thermo-electric cooled headgear comprising:
   (a) a hard shell having a cavity defined in and through said hard shell;
   (b) thermo-electric heat pump means mounted in said cavity in such a manner that said heat pump means does not significantly protrude into the head-accommodating space defined by said hard shell;
   (c) thermal radiation means closing said cavity and extending along a portion of the exterior of said shell, said thermal radiation means being connected to said heat pump means whereby heat is transferred by said heat pump means through said cavity and from said heat pump means for heat radiation from said radiation means;
   (d) insulated electrical conduction means operationally connected to said heat pump means and connectable to an electrical power source for energizing said heat pump to electrically pump heat to said radiation means; and,
   (e) liquid heat transfer means mounted in said headgear for transfering heat between a wearer's head and said heat pump, said liquid heat transfer means comprising bladder means conformable in shape to the contour of a wearer's head, said bladder means being fillable with a heat transfer liquid whereby heat transfer liquid convection currents transfer heat from the wearer's head, around said contour, and to said heat pump means.

* * * * *